United States Patent [19]

Sawa

[11] 4,305,398
[45] Dec. 15, 1981

[54] EYE FUNDUS OXIMETER

[75] Inventor: Seiji Sawa, Sakai, Japan

[73] Assignee: Minolta Camera Kabushiki Kaisha, Osaka, Japan

[21] Appl. No.: 141,081

[22] PCT Filed: Dec. 27, 1978

[86] PCT No.: PCT/JP78/00069

§ 371 Date: Aug. 22, 1979

§ 102(e) Date: Aug. 22, 1979

[87] PCT Pub. No.: WO79/00465

PCT Pub. Date: Jul. 26, 1979

[51] Int. Cl.³ .............................................. A61B 5/00
[52] U.S. Cl. .................................... 128/633; 128/666; 128/745; 356/41
[58] Field of Search ............... 128/633, 665, 666, 745; 356/39-41

[56] References Cited

U.S. PATENT DOCUMENTS

| | | | |
|---|---|---|---|
| 3,638,640 | 2/1972 | Shaw | 356/41 X |
| 3,647,299 | 3/1972 | Lavallee | 356/41 |
| 3,799,672 | 3/1974 | Vurek | 356/41 |
| 3,802,776 | 4/1974 | Tchang | 356/41 |
| 3,804,535 | 4/1974 | Rodriguez | 356/41 X |
| 4,086,915 | 5/1978 | Kofsky et al. | 128/633 |
| 4,167,331 | 9/1979 | Nielsen | 128/633 X |

OTHER PUBLICATIONS

Cohen, A. J. et al., *I.E.E.E. Trans. on Biomed. Engng.*, vol.-BME 23, No. 5, pp. 391-400, Sep. 1976.
Laing, R. A. et al., *I.E.E.E. Trans. on Biomed. Engng.*, vol.-BME 22, No. 3, pp. 183-195, May 1975.
Broad Foot, K. D. et al., Brit. J. Ophthal. (1961) 45, 161-182.

*Primary Examiner*—Kyle L. Howell
*Attorney, Agent, or Firm*—Jackson, Jones & Price

[57] ABSTRACT

An eye fundus oximeter adapted to measure spectrally the oxygen saturation of the blood in the fundus of the human eye. The oximeter includes an illuminating optical system (8, 21, 10) for first illuminating the fundus of the patient's eye (11) with light of a wide wavelength range and then illuminating the same with light of four different spectra, a photoelectric element (13) for receiving the four kinds of light directly and not via the patient's eye and a photoelectric element (16) for receiving the four kinds of light impringing on the fundus of the eye and then reflected therefrom. The outputs of these photoelectric elements (13, 16) are compared at each of the same spectra, the results of such comparison being subject to given arithmetic operations to evaluate the oxygen saturation. The purpose of the pre-illumination of the eye fundus with light of a wide wavelength range is to discolor visual pigments in the photoreceptor cell layer in the fundus and aid in deriving information about the blood in the fundus.

16 Claims, 7 Drawing Figures

4,305,398

EYE FUNDUS OXIMETER

TECHNICAL FIELD

This invention relates to an eye fundus oximeter which measures photoelectrically the oxygen saturation of the blood in the fundus of the eye.

BACKGROUND

Measurements of the oxygen saturation of the blood in the fundus of the eye are very instrumental for prevention and diagnosis of geriatric brain diseases such as hypertension and arterial sclerosis and also for premature infant monitoring.

In order to obtain information about the blood in the eye fundus, it is not sufficient to merely know the status of blood vessels in the eye fundus and thus necessary to carry on spectral analysis. In the case of this type of analysis, however, great difficulties are expected in discriminating the reflection or absorption of light by the eye fundus blood from the reflection of light on the surfaces of the cornea and the crystalline lens or absorption of light by various cell layers in the eye fundus. Accordingly, there has been no prior art device available which could measure the oxygen saturation of the blood in the eye fundus.

DISCLOSURE OF THE INVENTION

It is therefore an object of the present invention to obviate the above discussed measurement difficulties and enable measurements of the percentage oxygen saturation of the blood in the fundus of the eye. Pursuant to the operating principle of the present invention, the phenomenon in which visual pigments in a layer of photoreceptor cells may discolor and become transparent upon illumination of light is utilized and the influences of surfacial reflection about the cornea, the crystalline lens and so forth and absorption of light in cell layers in the eyefundus are removed by performing arithmetic operation on measurements utilizing four different wavelengths of light.

As described briefly above, the present invention obviates optical influences of tissues other than the blood to dispense with any conpensation for personal differences, and makes it possible to trace changes in the oxygen saturation over the progress of time by its capability of prompt measurement.

PREFERRED EMBODIMENTS OF THE INVENTION

Figure 1:
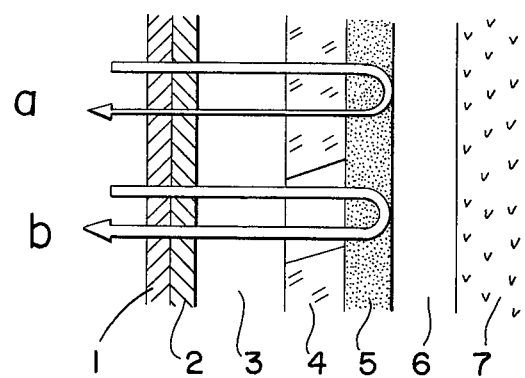
FIG. 1 is a cross sectional schematic view of eye fundus cell layers for illustration of the principle of the present invention.

FIG. 1 is a schematic representation of cell layers in the eye fundus for explanation of the operating principle of the present invention. There are illustrated blood vessel layers 1 and 2 containing oxided hemoglobin and reduced hemoglobin, a layer 3 consisting of nerve fibers and ganglian cells, a photoreceptor cell layer 4, a pigment epithelium layer 5, the choroid 6 and the sclera 7. In FIG. 1, the left handed side thereof corresponds to the front side of the eye. Light impinges on the photoreceptor cell layer 4 through the blood vessel layers 1 and 2 and the nerve fiber and ganglian cell layer 3. Visual pigments contained in the photoreceptor cell layer 4 tend to discolor upon illumination of eye intensity light, in other words, the absorption band thereof is shifted from a visual range to an ultraviolet range so that the visual pigments become transparent with respect to the visual range. The intensity of light reflected from eye fundus is very small if the light is incident upon the portion of the eye fundus where illuminating light has not been previously applied and the photoreceptor cell layer does not discolor, since a greater part of the incident light in this case is absorbed by the photoreceptor cell layer 4 and the intensity of light returning from reflection on the pigment epithelium layer 5, the choroid 6, etc., is very small. This light is indicated by a reduced arrow schematic "a" in FIG. 1. By contrast, measurement light incident upon the portion of the eye wherein a quantity of illuminated light had been previously applied to bring about that discoloring phenomenon in the photoreceptor cell layer 4 is not substantially absorbed by this layer 4, thus traveling through and being reflected from the pigment epithelium layer 5, the choroid 6, etc. as shown by schematic arrow "b" in FIG. 1. Since this light passes through the blood vessel layers 1 and 2 twice, it is subject to absorption by hemoglobin and comes to carry information about the blood. Accordingly, the eye fundus is illuminated with four different wavelengths of light and reflected lights therefrom are employed for spectral analysis under the conditions where flashes of light with high intensity have been previously applied to the eye fundus for a short period of time to cause the discoloring phenomenon of the photoreceptor cell layer 4 and this discoloring phenomenon remains.

The absorption coefficients of the respective layers 1 to 5 in FIG. 1 at a specific wavelength of light are denoted as $K_1$, $K_2$, $K_3$, $K_4$ and $K_5$ and the thickness thereof as $l_1$, $l_2$, $l_3$, $l_4$ and $l_5$. The suffixes correspond to the reference numbers of the respective layers of FIG. 1. The intensity $I''$ of light received by a measuring instrument can be written as follows;

$$I'' = \alpha I' + I' \exp(-2K_1 l_1 - 2K_2 l_2 - 2K_5 l_5)$$

wherein $I'$ represents the intensity of the incident light directed towards the eye and $\alpha$ represents the efficiency of the incident light which actually returns to the measuring instrument after scattering and reflection from the eye, that is, the cornea and crystalline lens. Thus, the first term of the righthand side of the above equation corresponds to the intensity of the light reflected from the eye surface back to the measuring instrument while the second term refers to that portion of the intensity of light that has been transmitted into and returns from the interior of the eye and has been affected by the abovementioned layers. Since the absorption coefficient of the nerve fiber and ganglian cell layer 3 is substantially zero and the counterpart of the photoreceptor cell layer 4 is negligible when the same is subject to the previous light illumination and manifests the discoloring phenomenon, the above formula lacks items regarding $K_3 l_3$ and $K_4 l_4$. In the formula defined above the respective absorption coefficients are known and four factors $\alpha$, $l_1$, $l_2$ and $l_5$ are unknown. The four unknown factors can be evaluated by applying the above defined formula to the intensity of the incident light and the intensity of the light reaching the measuring instrument at the four different wavelengths of light, respectively. The values necessary for evaluating the oxygen saturation of the blood in the eye fundus are the thicknesses $l_1$ and $l_2$ of the blood vessel layers 1 and 2. If the absorption coefficients of the respective layers at the four wavelengths of light are labelled $K_{11}$, $K_{21}$, $K_{31}$, $K_{41}$ and so forth (the first digit of the suffixes identifies the wavelengths and the second identifies the layers), then the following relationships will stand between the intensities $I_1'$, $I_2'$, $I_3'$ and $I_4'$ of the incident light and the intensities $I_1''$, $I_2''$, $I_3''$ and $I_4''$ of the light entering the measuring instrument. It will be noted that $\alpha$ and the absorption coefficient $K_5$ of the pigment epithelium layer 5 are not dependent upon wavelength and constant for an overall range of wavelength of light.

$I_1'' = \alpha I_1' + I_1' \exp(-2K_{11}l_1 - 2K_{12}l_2 - 2K_5l_5)$
$I_2'' = \alpha I_2' + I_2' \exp(-2K_{21}l_1 = 2K_{22}l_2 - 2K_5l_5)$
$I_3'' = \alpha I_3' + I_3' \exp(-2K_{31}l_1 - 2K_{32}l_2 - 2K_5l_5)$
$I_4'' = \alpha I_4' + I_4' \exp(-2K_{41}l_1 - 2K_{42}l_2 - 2K_5l_5)$ If $I_1''/I_1' = I_1$, $I_2''I_2'/ = I_2$, etc., then $$\frac{I_1 - I_3}{I_1 - I_4} = \frac{\exp(-2K_{11}l_1 - 2K_{12}l_2) - \exp(-2K_{31}l_1 - 2K_{32}l_2)}{\exp(-2K_{11}l_1 - 2K_{12}l_2) - \exp(-2K_{41}l_1 - 2K_{42}l_2)}$$

$$\frac{I_2 - I_3}{I_2 - I_4} = \frac{\exp(-2K_{21}l_1 - 2K_{23}l_2) - \exp(-2K_{31}l_1 - 2K_{32}l_2)}{\exp(-2K_{21}l_1 - 2K_{22}l_2) - \exp(-2K_{41}l_1 - 2K_{42}l_2)}$$

The above formulas are all defined as a function of $l_1$ and $l_2$. In relation to the fact that oxidized hemoglobin and reduced hemoglobin are practically mixed in the blood, the thicknesses $l_1$ and $l_2$ of the layers 1 and 2 are defined by assuming that only oxidized hemoglobin is gathered to form layer 1 separately from reduced hemoglobin which is by itself gathered to form layer 2, and that the thickness of layers 1 and 2 are representative of the amount of only oxidized hemoglobin and that of only reduced hemoglobin, respectively. Therefore, the oxygen saturation $SO_2$ of the blood in the eye fundus can be written as follows:

$$SO_2 = \frac{100 \times l_1}{l_1 + l_2}$$

Thus, the oxygen saturation can be evaluated by preparing various cases of values of the above defined two formulas which can be calculated in advance under various assumptions of the coefficients $K_{11}$, etc., and the oxygen saturation and by retroactively identifying a desired oxygen saturation through a set of the prepared values which is equal to actually measured values $(I_1 - I_3)/(I_1 - I_4)$ and $(I_2 - I_3)/(I_2 - I_4)$. This is the conceptional principle of the present invention. In practice, the identification of the oxygen saturation through the actual measurement results is dependent upon a function of a computer.

The present invention will now be described in more detail in terms of its embodiment.

Figure 2:
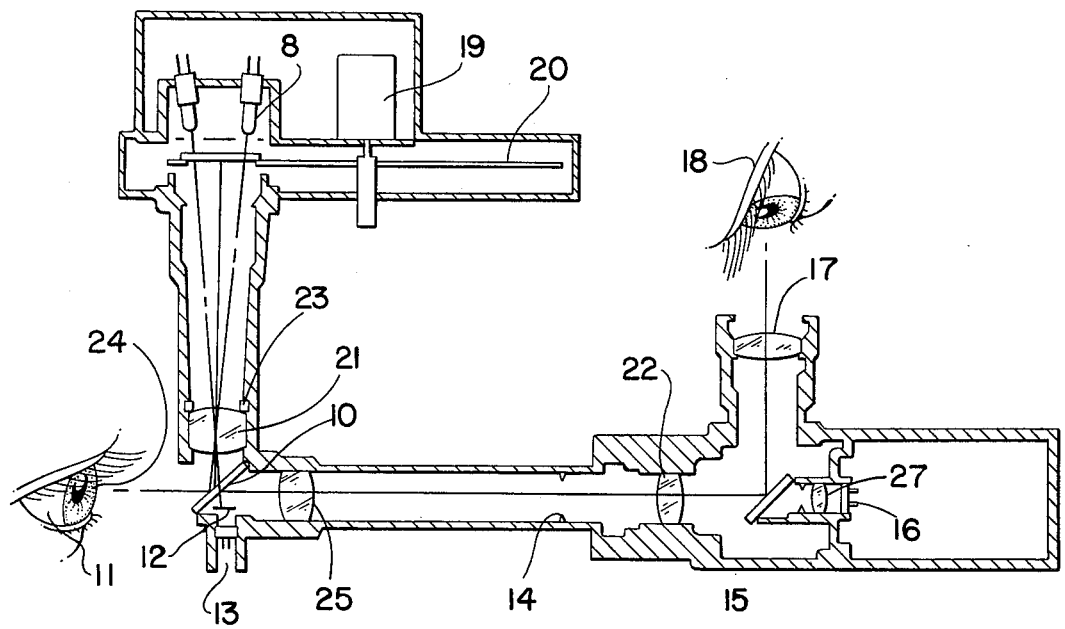
FIG. 2 is an elevational cross sectional side view of an optical system according to one embodiment of the present invention.
Figure 3:
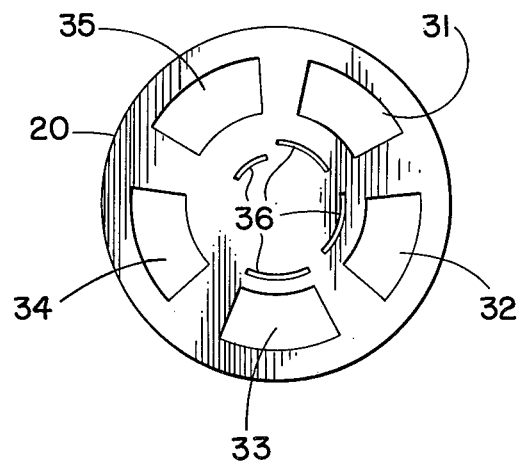
FIG. 3 is a plan view of a filter disc.
Figure 4:
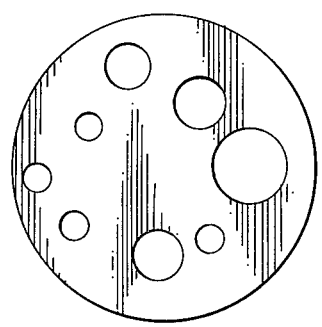
FIG. 4 is a plan view of apertured disc.

FIG. 2 shows one embodiment of the present invention, in which the eye to be examined is labeled 11 and a light source for illuminating the eye fundus with light is labeled 8. A disc 20, as indicated in FIG. 3, has five sector-shaped windows 31-35 one of which is merely an opening as denoted as 31 and the other four windows 32-35 carry filters having different wavelengths for transmission. The disc 20 is rotated by a motor 19. The window 31 in the disc enables an overall quantity of light from the light source 8 to pass therethrough to previously illuminate the eye fundus with light for the development of the discoloring phenomenon in the photoreceptor cell layer, whereas the other four windows 32-35 aid in illuminating the eye fundus with the four different wavelengths of light. A lens 21 is used to focus an image of the light source 8 on the cornea 24 of the patient's eye 11, thus leading light to the eye fundus. A portion of light emerged from the light source 8 traverses a translucent mirror 10 and impinges on a light receiving photodiode 13 which in turn provides information of the above discussed incident light intensities $I_1''$, $I_2''$, $I_3''$ and $I_4''$. The light receiving element 13 is located so as to be conjugate with the cornea 24 with respect to the translucent mirror 10. A neutral density filter 12 is disposed in front of the light receiving element 13 to keep a linear relationship between current and illumination. An aperture 14 on an optical axis extending toward the right side of the patient's eye 11 is located so as to be conjugate with the retina of the patient's eye 11 with respect to a lens 25 to effectively allow the passage of reflected light from the retina but prohibit the passage of reflected and scattering light from the cornea 24 wherever practicable. Thus an improved S/N ratio is ensured since the reflected light from the retina is relatively weak. Thereafter, the reflected light from the retina is focused via a couple of lenses 22 and 27 on a light receiving element which is practically a photodiode 16. The output of the light receiving element 16 bears information indicative of the above discussed values $I_1'$, $I_2'$, $I_3'$ and $I_4'$. The viewer's eye 18 is located to observe an image of the retina in the eye fundus of the patient's eye through a translucent mirror 15 and an eyepiece 17. An aperture 23 having various holes as in FIG. 4 is disposed in front of the lens 21 to enable one of the various portions of the eye fundus to be selectively illuminated with light. The disc 20 is further provided with arc-shaped slits 36 which correspond to respective windows 31-35. A photoelectric device although not shown in the drawings is adapted to sense the arrival of the slits and provide synchronizing signals for discriminating the outputs of the light receiving elements 13 and 16 at each wavelength.

Figure 5:
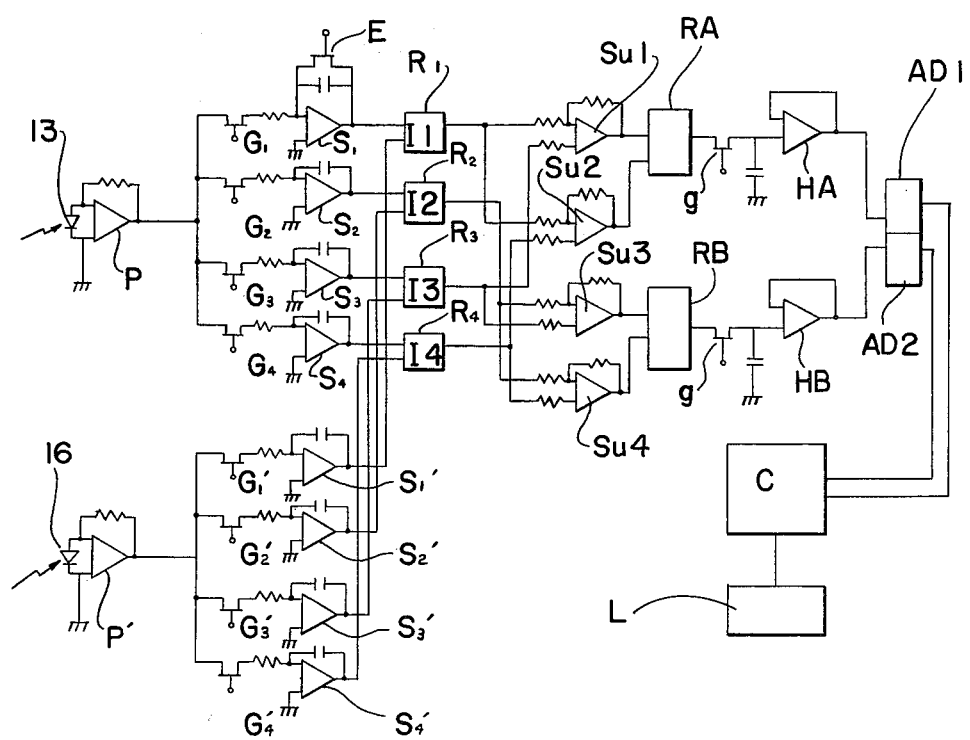
FIG. 5 is a circuit diagram of an arithmetic operation circuit according to one embodiment of the present invention.

FIG. 5 illustrates a circuit structure for evaluating $(I_1 - I_3)/(I_1 - I_4)$ and $(I_2 - I_3)/(I_2 - I_4)$. $I_1$, $I_2$, etc are ratios of the intensities $I_1''$, $I_2''$, etc. of the light reflected from the retina to the intensities $I_1'$, $I_2'$, etc. of the incident light on the eyeball, respectively, and equal to the output of the light receiving element 16 divided by the output of the light receiving element 13. In FIG. 5, both the elements 13 and 16 correspond to those in FIG. 2, of which the output currents are converted into voltage signals via current to voltage converters P and P', respectively. The voltage signals are applied to integrators $S_1$-$S_4$ and $S_1'$-$S_4'$ via gates $G_1$-$G_4$ and $G_1'$-$G_4'$.

The gates $G_1$ and $G_1'$ are open while the filter secured on the window 32 of FIG. 3 is in front of the light source 8, similarly the gates $G_2$ and $G_2'$ open for the filter on the window 33, the gates $G_3$ and $G_3'$ open for the filter on the window 34, and the gates $G_4$ and $G_4'$ for the filter on the window 35, respectively. The outputs of the respective light receiving elements are amplified and then held through the integration operation. E is a reset gate, a similar reset gate being provided for each of the integrators although not shown because of its space requirement in the drawing. The outputs of the respective integrators are representative of $I_1'$-$I_4'$ and $I_1''$-$I_4''$ and are supplied respectively to dividers $R_1$-$R_4$ for evaluating $I_1'/I_1'$ (=$I_1$), etc. and thus $I_1$ through $I_4$. The outputs of $R_1$-$R_4$ are fed to subtractors $Su_1$-$Su_4$ to calculate $(I_1-I_3)$, $(I_1-I_4)$, $(I_2-I_3)$ and $(I_2-I_4)$, the resulting outputs being fed to dividers $R_A$ and $R_B$ to calculate $(I_1-I_3)/(I_1-I_4)$, etc. The calculation results are stored in sample hold circuits HA and HB through the gate g which becomes open after a predetermined number of revolutions of the disc 20, and converted into digital signals via $AD_1$ and $AD_2$ and eventually sent to a computer C.

Figure 6:
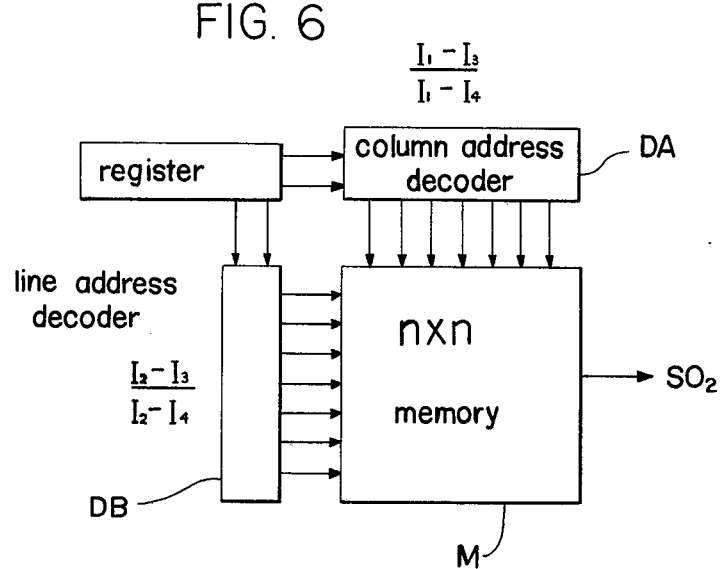
FIG. 6 is a basic block diagram of the interior of a computer.

FIG. 6 shows the internal structure of the computer C in which the outputs of $AD_1$ and $AD_2$ are applied to decoders DA and DB, the respective values $(I_1-I_3)/(I_1-I_4)=A$ and $(I_2-I_3)/(I_2-I_4)=B$ specifying a column address and a line address of an $n \times n$ memory M. The $n \times n$ memory contains a number of pre-calculated oxygen saturation values according to various combinations of A and B. The memory is read out as if a desired oxygen saturation is evaluated from the actually measured values A and B while the viewer consults with a lookup table plotted with various values A as the axis of abscissa and various values B as the axis of ordinate. The read out oxygen saturation is displayed on a display device L.

Figure 7:
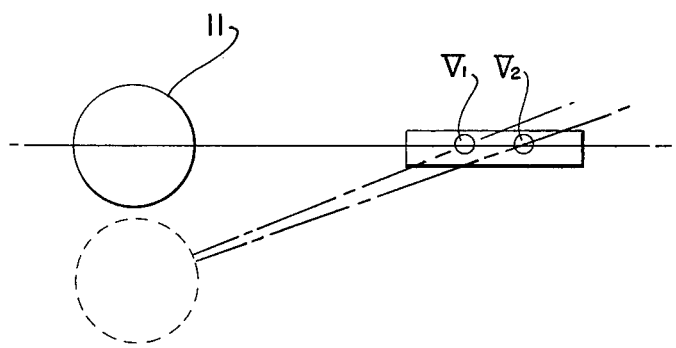
FIG. 7 is a plan view of an example of a device for preventing the movement of the eye to be examined.

Movement of the eye or the head, which is reasonably expected, may be an obstacle in steadily illuminating a specific area of the eye fundus with light and measuring reflected light therefrom. For this reason, as shown in FIG. 7, targets of collimation $V_1$ and $V_2$ are disposed along the line of vision of the patient's eye so that the patient may fixed his eye so as to observe $V_1$ and $V_2$ as if they were a single target. Thus, the movement of eye or head can be substantially prevented to a degree sufficient for the purpose of measurement and this condition is also capable of being sufficiently maintained for a time period required for the measurement.

I claim:

1. An eye fundus oximeter comprising: an optical system for separately and sequentially illuminating the fundus of the eye with at least four specific wavelengths of light and transmitting reflected light from the fundus of the eye to a first light receiving element; a second light receiving element for receiving the light in a condition prior to its incidence upon said first light receiving element and the patient's eye; means for illuminating the fundus of the eye with a light of high power including at least the predetermined four wavelengths, prior to a separate and sequential illumination by at least four specific wavelengths of light, to make the photoreceptor cells in the eye fundus substantially transparent with respect to the four specifice wavelengths of light; means for deriving and discriminating the outputs of the two light receiving elements at each of the at least four different wavelengths of light, respectively, and an arithmetic operation circuit performing operations on the two outputs of the at least four different wavelengths, respectively.

2. An eye fundus oximeter according to claim 1 wherein said operation circuit comprises a divider for calculating $I_1=I_1'/I_1''$, $I_2=I_2'/I_2''$, $I_3=I_3'/I_3''$ and $I_4=I_4'/I_4''$ wherein $I_1'$, $I_2'$, $I_3'$ and $I_4'$ are the intensities of the reflected light from the fundus of the patient's eye at the four different wavelengths of light and $I_1''$, $I_2''$, $I_3''$ and $I_4''$ are the intensities of the intensities of light before impinging on the patient's eye, a subtractor for calculating $(I_1-I_3)$, $(I_1-I_4)$, $(I_2-I_3)$ and $(I_2-I_4)$ based upon the outputs $I_1$-$I_4$ of said divider and a divider for calculating $A=(I_1-I_3)/(I_1-I_4)$ and $B=(I_2-I_3)/(I_2-I_3)$ based upon the output of said subtractor, thereby identifying one of the oxygen saturation values, which are preparatory calculated, in response to the values A and B.

3. An eye fundus oximeter according to claim 1 or claim 2 further comprising a computer wherein the values A and B are decoded into a column address specifying signal and a line address specifying signal for a memory from which an oxygen saturation is read out according to the values A and B and placed on a display.

4. An eye fundus oximeter comprising:
   means for directing at least four preselected wavelengths of source light to an object eye;
   means for receiving the source light reflected from the object eye;
   means, responsive to said receiving means, for generating measurement signals representative of the intensity of reflected light with respect to the preselected wavelengths, respectively;
   means for varying the wavelength transmission characteristic of the eye fundus, before the direction to and receiving of said four preselected wavelengths of source light from the object eye to generate measurement signals, to make the photoreceptor cell in the eye fundus substantially transparent with respect to said preselected wavelengths of light, and
   means, connected to said generating means, for calculating an oxygen saturation of the blood in the eye fundus from said measurement signals.

5. The invention of claim 4 further comprising means for detecting the intensity of said source light with respect to said preselected wavelengths, respectively, wherein said calculating means comprises means, connected to said generating means and to said detecting means, for obtaining information relating to the light absorption by the eye fundus with respect to said preselected wavelengths, respectively.

6. The invention of claim 5, wherein the means for varying the wavelength transmission characteristic includes means for illuminating the eye fundus with a high power of light including all the preselected wavelengths prior to a measurement sampling with the preselected wavelengths.

7. The invention of claim 6 further comprising means, responsive to said directing means, for identifying the wavelength which is actually directed, and for relating an identification of the wavelength of the signals from the generating means and the intensity detection of the detecting means.

8. The invention of claim 4, wherein said preselected wavelengths consist of four different wavelengths.

9. The invention of claim 4 further comprising means for detecting the intensity of said source light with respect to each of said preselected wavelengths, and wherein said calculating means comprising means for calculating the following values, A and B:

$$A = (I_1''/I_1' - I_3''/I_3')/(I_1''/I_1' - I_4''/I_4')$$
$$B = (I_2''/I_2' - I_3''/I_3')/(I_2''/I_2' - I_4''/I_4')$$

wherein: $I_1'$ to $I_4'$ represent the intensity of the source light detected by said detecting means with respect to a first to fourth wavelength, respectively; and $I_1''$ to $I_4''$ represent intensity of the reflected light received by said receiving means, which correspond to the signals of said generating means with respect to said first to fourth wavelengths of light, respectively.

10. The invention of claim 9, wherein said calculating means further comprises means for preparatory storing a variety of predetermined values of oxygen saturation and means for identifying one of said oxygen saturation values in response to said values, A and B.

11. The invention of claim 10 wherein said storing means stores said variety of oxygen saturation values at corresponding addresses to be determined by a pair of address codes, respectively, and said identifying means comprising means for decoding said values, A and B into a pair of address codes to determine one of said addresses and to read out an oxygen saturation value stored therein.

12. The invention of claim 4 further comprising a pair of visual targets of collimation disposed along a line of sight with which the optical axis of the object eye is to be coincided.

13. The invention of claim 4 wherein the means for varying the wavelength transmission characteristic includes a flash of high intensity light for a short period of time prior to measurement sampling with the preselected wavelengths.

14. The invention of claim 4 wherein said means for directing source light comprises means for successively and separately transmitting said preselected wavelengths of light when the photoreceptor cells have been made relatively transparent to said preselected wavelengths.

15. The invention of claim 14 further comprising means, responsive to said transmitting means, for identifying the wavelength corresponding to the measurement signals.

16. The invention of claim 4 further comprising means for controlling the sequence of illuminating the eye fundus and directing the source light to the eye so that said preselected wavelengths of light are successively and separately transmitted to the eye following the rendering of the eye fundus substantially transparent.

* * * * *